United States Patent [19]

Burtscher et al.

[11] Patent Number: 4,769,548
[45] Date of Patent: Sep. 6, 1988

[54] METHOD FOR THE QUANTITATIVE AND QUALITATIVE CHARACTERIZATION OF SUBSTANCES CONTAINED IN A GASEOUS CARRIER MEDIUM

[76] Inventors: Heinz K. Burtscher, Zimmergasse 5, CH-8000 Zürich, Switzerland; Reinhard R. Niessmer, August-Lämmle-Weg 7, D-7200 Tutthingen, Fed. Rep. of Germany; Andreas Schmidt-Ott, Kürbergsteig 7, CH-8049 Zurich; Hans C. Siegmann, Kurbergstr. 24, both of CH-8049 Z,e,uml/u/ rich, Switzerland

[21] Appl. No.: 876,678

[22] Filed: Jun. 20, 1986

Related U.S. Application Data

[63] Continuation of Ser. No. 743,438, Jun. 11, 1985, abandoned.

[30] Foreign Application Priority Data

Jun. 14, 1984 [DE] Fed. Rep. of Germany ....... 3422053

[51] Int. Cl.$^4$ ............................................. G01N 27/64
[52] U.S. Cl. ................................ 250/423 P; 324/464; 436/153
[58] Field of Search .............. 250/423 P, 432 R, 372, 250/304, 379; 324/464, 465; 436/153, 181; 422/98

[56] References Cited

U.S. PATENT DOCUMENTS 4,574,004 3/1986 Schmidt-Ott et al. .......... 250/423 P

OTHER PUBLICATIONS

Burtscher et al, "Probing Aerosols by Photoelectric Charging", J. Appl. Phys., 53(5), May 1982, pp. 3787-3791.

Primary Examiner—Carolyn E. Fields
Attorney, Agent, or Firm—Tarolli, Sundheim & Covell

[57] ABSTRACT

The invention provides a method for the quantitative and/or qualitative characterization of substances which are contained in a gaseous carrier medium. Modifications of the surface of small solid particles suspended in a carrier gas may be measured with very high sensitivity by the application of the photoelectric effect. Thereby, an aerosol is chemically modified, e.g. by admixing a gaseous agent or a gas mixture, or by subjecting it to an electromagnetic radiation, and subsequently the resulting variation of the photoelectron emission from the suspended particles is recorded. By measuring the variation of the photoelectric effect during the admixing or variation of a gaseous agent to the aerosol to be examined or during a variation of the electromagnetic radiation, to which the aerosol to be examined is subjected, the suspended particles may be classified in one or several steps. On the other hand, the method may be useful as well for the detection and characterization of gases or gas traces in a carrier gas by admixing artificially created solid particles of known composition and nature to the gaseous substance to be examined.

12 Claims, 2 Drawing Sheets

METHOD FOR THE QUANTITATIVE AND QUALITATIVE CHARACTERIZATION OF SUBSTANCES CONTAINED IN A GASEOUS CARRIER MEDIUM

This is a continuation of co-pending application Ser. No. 743,438, filed on June 11, 1985, now abandoned.

BACKGROUND OF THE INVENTION

1. Field of the Invention

The present invention refers to a method for the quantitative and/or qualitative characterization of substances contained in a gaseous carrier medium, e.g. for detecting the nature and/or the amount of small solid particles contained in a carrier gas, or for detecting the presence of an unknown gas in a carrier gas etc. Particularly the invention refers to a method of the aforementioned kind in which small solid particles suspended in a carrier gas and unknown gases or gas traces possibly contained in the carrier gas are detected and characterized by admixing an agent to the carrier gas to be examined or by effecting a photochemical reaction in the carrier gas to be examined.

2. Prior Art

The well known photoelectric effect, being a surface sensitive method, is very well suited to furnish evidence of even the slightest chemical modification of the surface of small solid particles. Particularly the photoelectric yeild (i.e. the rate of electron emission divided by the intensity of the radiation) is sensitively changed even by adsorbant layers on the surface of the particles which have but a monoatomic or monomolecular thickness. A similar effect may be observed if the surface of the particles is modified by a chemical reaction. The photoemission from small solid particles suspended in a gaseous carrier may be used to detect and characterize a chemical modification of the surface of these particles. Usually it is understood that small solid particles suspended in a gaseous carrier have a diameter in a range between 1 nm and 10 $\mu$m. They have the property to remain suspended in the gaseous carrier, depending of their size for a longer or shorter period. Such a suspension, i.e. a carrier gas containing suspended small solid particles, is known as an aerosol.

Upon the photoemission from suspended particles contained in a gaseous suspension, the particles having a positive charge are left. The electrons diffuse in the gas and usually form negative ions. Evidence of such microscopic charge separation may be proved according to different methods. One of the known methods is disclosed in reference (1) and is designated as measurement of the aerosol photo conductance. Thereby the conductance of the gas within an electric alternating current field is measured. Other known methods are based on the principle that a different diffusion rate or mobility of the photoelectrons or of the ions generated therefrom as compared to the particles results in a macroscopic charge separation, so that the positive and/or the negative charges may be determined separately. According to reference (2), the electric current generated by the photoelectrically positively charged, continuously flowing particles is measured, after the photoelectrons have been removed from the aerosol by diffusion and drift in the electric field.

OBJECTS OF THE INVENTION

It is an object of the invention to provide an improved method which may be performed much easier than the previously known methods, but nevertheless ensures a detection and/or characterization of substances which are present even in extremely low concentration.

It is a further object of the invention to provide a method of detecting the amount of small solid particles suspended in an aerosol with high accuracy, even if the aerosol to be examined has a very low concentration of these particles. It is a still further object of the invention to provide a method to characterize the nature of small solid particles suspended in the aerosol, even if the aerosol to be examined has a very low concentration of these particles.

A still further object of the invention is to provide a method to detect a gas, a gas mixture or gas traces, even in very low concentration, that may be present in a gaseous carrier, and to measure the amount thereof as well as to characterize its nature.

SUMMARY OF THE INVENTION

In order to determine the amount of small solid particles contained in an aerosol or the nature thereof, the aerosol is exposed to an ultraviolet radiation or to an X-ray radiation, thereby producing charge carriers generated by photoemission from the small solid particles. Then the photoelectron emission is measured. This can be done by measuring the charge of the charge carriers or the current generated by the charge of the charge carriers. The result of this measurement is recorded as a first measurement value.

In a second step, the surface of the small solid particles contained in the aerosol is modified in a suitable manner, e.g. chemically modified, and the aerosol with the particles having a modified surface is exposed to an ultraviolet radiation or to an X-ray radiation again. The resulting photoelectron emission is measured as hereinbefore explained and the result of this measurement is recorded as a second measurement value.

Now the first and the second measurement values are compared and therefrom the nature and/or amount of the small solid particles contained in the aerosol to be examined can be determined.

Sometimes it might be useful if the step of modifying the surface of the particles is repeated once or several times and the measuring step is subsequently performed to get a third or a number of further measurement values. The plurality of measurement values thus obtained and recorded are then compared to determine the nature and/or amount of the small solid particles contained in the aerosol to be examined.

In order to determine the presence and/or the amount of a gas or a gas mixture possibly contained in a gaseous carrier substance, and in order to characterize the nature of the gas or gas mixture thus recognized, the gaseous substance is mixed with small solid particles of known composition in order to produce an aerosol and this aerosol is exposed to an ultraviolet radiation or to an X-ray radiation, thereby producing charge carriers generated by photoemission from the small solid particles. The photoelectron emission may then be measured by measuring the charge of the charge carriers or the current generated by the charge of the charge carriers, and the result of this measurement is recorded as a first measurement value.

In a further step, the surface of the small solid particles contained in the aerosol is modified as explained hereinabove, and the aerosol containing said small solid particles having a modified surface is exposed to an ultraviolet radiation or to an X-ray radiation again. The photoelectron emission is measured in a corresponding way and the result of this measurement is recorded as a second measurement value.

Finally said first and said second measurement values are compared and therefrom the nature and/or amount of the gaseous substance to be examined and contained in the aerosol is determined.

As already explained hereinbefore, it might be useful in performing this method as well, if the step of modifying the surface of the particles is repeated once or several times and the measuring step is subsequently performed to get a third or a number of further measurement values. The plurality of measurement values thus obtained and recorded are then compared to determine the nature and/or amount of the gaseous substance contained in the aerosol to be examined.

In the known methods as disclosed in reference (1) and reference (2) a signal is measured which is proportional to the photoelectric yield. According to the present invention, however, the variation of the signal may be recorded which results from a modification of the suspended particles, particularly from a chemical modification of the surface thereof. The modification of the surface of the particles may be obtained by admixing a gaseous substance which diffuses to the surface of the particle, or by exposing the aerosol to a suitable radiation, resulting in a photochemical modification of the surface of the particles, or by both measures simultaneously. A modification of the photoelectric activity of the particles effected in one of the above explained ways is typical as far as the chemical nature of the surface of the particles is concerned; it is thereby possible to analyze the nature of the particles on the basis of a measurement of the photoelectric activity or to classify the particles.

DESCRIPTION OF SOME EXAMPLES AND FURTHER DETAILS OF THE METHOD

A typical example of the application of the method according to the present invention is the characterization of 11-electron-enriched substances like polyaromatic hydrocarbons, which often occur in atmospheric aerosols, particularly on the surface of particles generated by the combustion of organic material. The comparatively high photoelectric activity of such compositions is decreased by addition reactions to conjugated or non-conjugated double or triple bonds. The oxidation of anthracene to anthraquinone by ozonization or the halogenization of polymethines may be cited as examples. Such photoelectric disactivations may be accelerated or even initiated in certain cases by exposing the aerosol to a radiation (photochemical disactivation). To this purpose either the same light source may be used as for the photoemission, or an additional radiation source may be used.

The addition of oxygen to perylene may be cited as an example of a photochemical disactivation. Perylene, in the presence of ozone, is photochemicaly disactivated under the influence of an ultraviolet radiation having a wavelength of 254 nm within a period of time, in which no disactivation at all can be proved without radiation. Besides the photochemical disactivation, a photochemic activation is possible as well.

If a disactivation or an activation by a photoemitting light source itself is not desired, such effect may be avoided e.g. by removing the corresponding gaseous reactants from the gas prior to the photoemission. This can be done by means of a diffusion separator, e.g. as it is disclosed in reference (3). Another possibility to suppress photochemical reactions during the photoemission may consist in keeping the radiation duration short. In the case of analyzing automotive exhaust gases, this has been successfully tried by using a xenon flash bulb with a flash impulse period of 2 ms; please cf. reference (4).

If an additional lamp is used to initialize the photochemical reaction, an undesired photoelectric charging of the particles may occur even during this step, if the applied light has a certain amount of radiation in the UV-region. However, subsequently, a well defined charge situation may be reinstated. A well known method therefor is the application of an aerosol neutralizer, as it is disclosed, e.g. in reference (5). By the application of such a neutralizer, positive and negative ions are generated in the gas under the influence of radioactive $\alpha$-, $\beta$-or $\gamma$-radiation, which recombine with the charge of the particles. Another possibility is to remove all particles, which are undesiredly charged, from the aerosol by means of an electric field and to collect them on electrodes. A neutralization of the aerosol prior to the step of photoemission may also be desired if the aerosol is already charged, either due to the nature of its generation or initially.

Another possibility to modify the aerosol specifically with regard to the substance may be seen in the step to expose the surface of the particles to a radiation without admixing any gaseous reactants. As an example, the photochemical dissociation of silverchloride may be cited, whereby particles consisting of elementary silver are obtained. The photoelectric activity is increased in this process.

The surface of the particles may be characterized, in one step or in several consecutive steps, if the gases to be admixed as agents and/or the spectra of the radiation for the photochemical modification and for the photoemission are chosen and varied in a suitable way.

Besides the characterization of aerosols, particularly the characterization of the small solid particles suspended in the gaseous carrier, the method according to the invention may be successfully used for determining the presence of a gas in a gaseous carrier and for the characterization of such gas, if present. To this purpose, the gaseous carrier, e.g. the atmospheric air, is mixed with an aerosol of predetermined, known composition. The photoelectric activity of the known aerosol will change because the gas to be detected or examined will adsorb to the particles of the known aerosol, thereby modifying the photoelectric behaviour of the particles in a certain manner which is typical for the gas to be characterized. With the method according to the present invention, gas traces may be detected with an extremely high sensitivity: The measuring limit corresponds approximately to one monolayer on ten particles each per $cm^3$, corresponding to $10^{-18}$ g/$cm^3$.

As an example, the detection of acetone or solvent vapor may be cited. Thereby an aerosol is used, which contains soot particles having a size of about 5 to 10 nm. The soot may easily generated by means of a gas flame. Alternatively carbon particles may be used which can be generated by an electric discharge between carbon electrodes or by means of a glowing carbon filament in an inert gas ambient.

BRIEF DESCRIPTION OF THE DRAWINGS

The enclosed drawings show embodiments of an apparatus suitable for performing the method according to the invention. In the following description, the method will be further explained, with reference to the drawings, in which:

FIG. 2 shows a schematic view of a further test set-up in order to perform the method of the invention to detect gas traces in a gaseous carrier, and FIG. 3 shows a schematic view of an addition to the apparatus according to FIG. 2.

DESCRIPTION OF THE PREFERRED EMBODIMENTS

Figure 1:
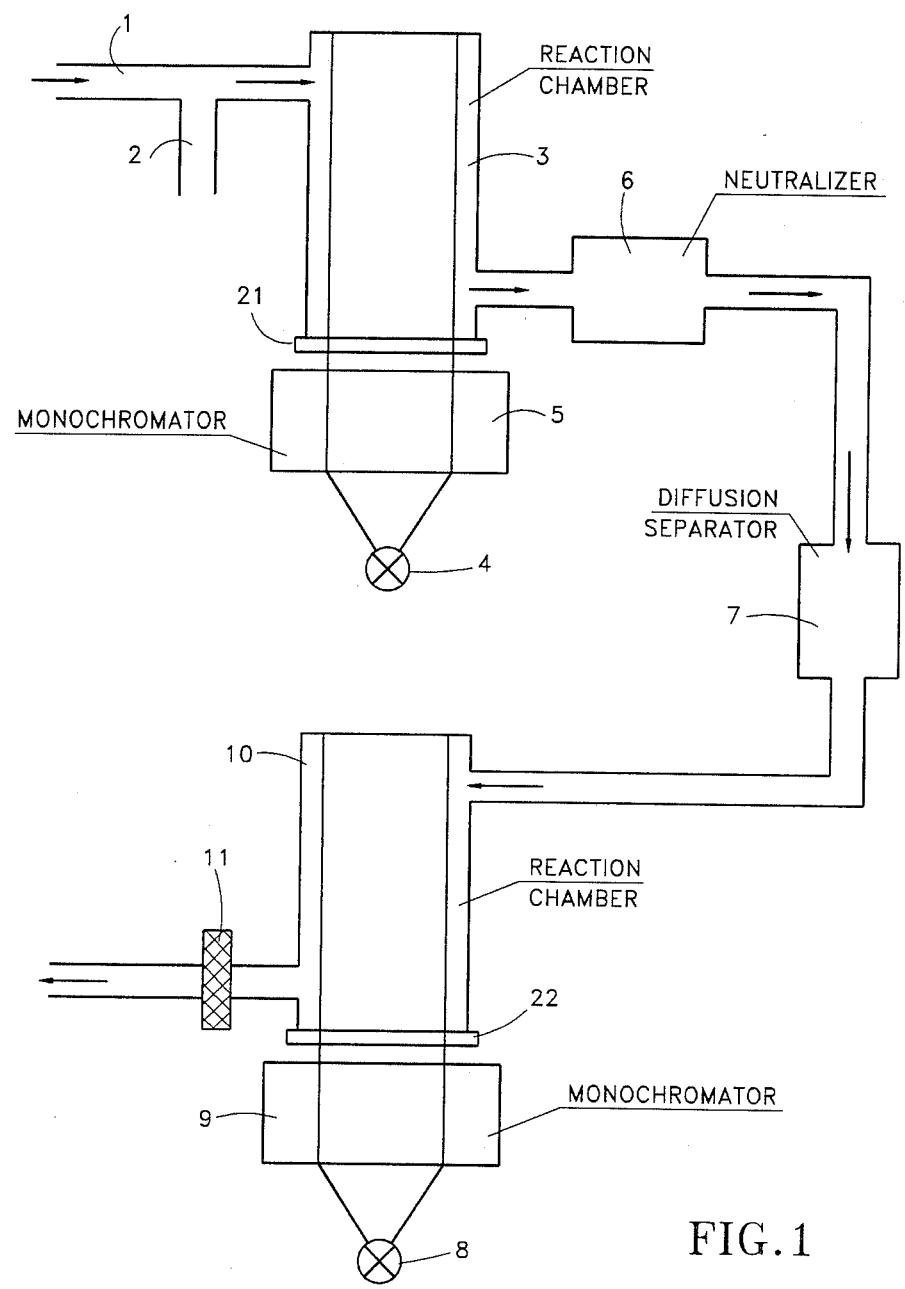
FIG. 1 shows a schematic view of a test set-up in order to perform the method of the invention to characterize small solid particles suspended in an aerosol flow.

With reference to the schematic view of an apparatus shown in FIG. 1, an example of performing the method according to the invention to characterize the particles suspended in an aerosol will now be further explained. The aerosol flow to be examined is fed through an inlet 1 and is mixed with a gaseous agent (a test gas) fed through a further inlet 2. This mixture enters a reaction chamber 3 which is exposed to an ultra violet light radiation with variable wavelength. The light is generated by a continuous mercury high pressure bulb 4, passes a monochromator 5 and enters the reaction chamber 3 through a window 21. The outlet of the reaction chamber 3 is connected to a neutralizer 6 which is adapted to neutralize the aerosol passing therethrough by means of a radioactive source ($Kr^{85}$ according to reference (5)). The output of the neutralizer 6 is connected to the input of a diffusion separator 7 which removes the remaining gaseous agent, which is not bond to the surface of the particles of the aerosol, and/or other gases, which could become photochemically active during a subsequent UV-radiation step.

Now the photochemical activity is determined. To this purpose, the aerosol, having left the diffusion separator 7, enters a further reaction chamber 10. Therein it is exposed to light which is generated by a pulsed xenon high pressure bulb 8, passing a further monochromator 9 and entering the reaction chamber 10 through a window 22. The aerosol finally leaves the reaction chamber 10 and passes a mechanical filter 11 arranged in the outlet port of the chamber 10, where the particles, which have been charged according to their photoelectric activity, are collected. Now the electric current generated by the charge carriers collected in the filter 11 may be measured and recorded as a first measurement value.

All the method steps as explained hereinbefore are then repeated, with the difference, that the admixture of the gaseous agent through the opening 2 is varied as far as its amount and/or nature is concerned, and/or the illumination of the reaction chamber 3 is switched on or off, or the intensity or the duration of the illumination is varied. All these variations result in a variation of the current which may be measured at the mechanical filter 11. These current variations, however, are typical for the nature of the substance to be examined. In this way, i.e. repeating the method steps several times, recording the measurement values of each step and comparing the measurement values, it is possible to characterize the nature of the particles contained in the aerosol to be examined.

Figures 2, 3:
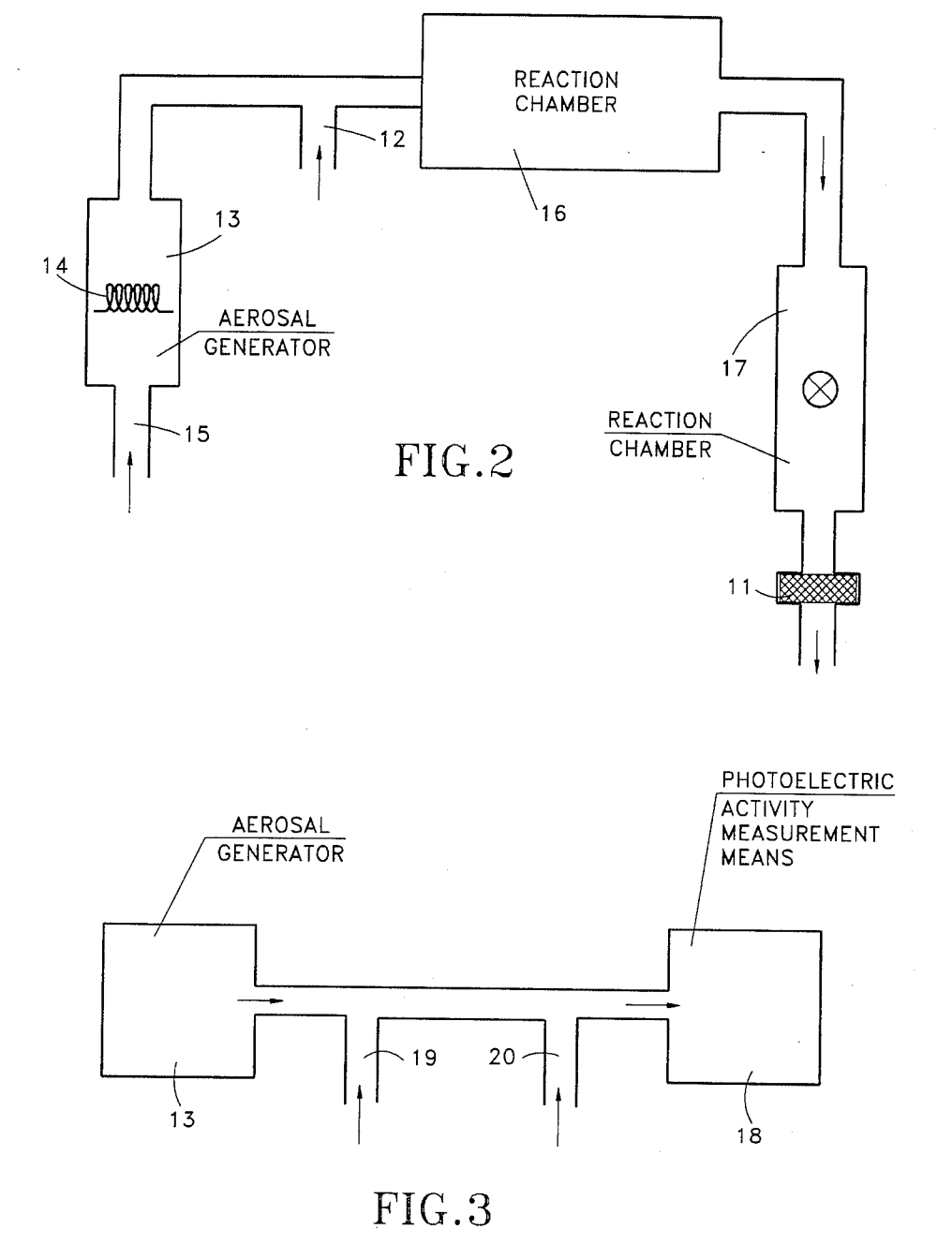

FIG. 2 shows schematically a test set-up to detect the presence of gases or gas traces in a gaseous carrier. A preferred field of application of this embodiment of the method according to the invention is e.g. the monitoring of the atmospheric at a working site with regard to the concentration of solvent vapors. Nitrogen is fed through an inlet 15 into an aerosol generator 13. The latter one comprises a carbon filament 14 arranged in its interior and which is connected to an electric current source, thereby emitting carbon particles which are suspended in the nitrogen to generate an aerosol of known composition and nature. The air or the gas to be examined is fed through an inlet 12 to a duct connecting the aerosol generator 13 to a reaction chamber 16 and is mixed therein with the aerosol previously generated in the aerosol generator 13. The mixture of air or gas fed through the inlet 12 and the artificially generated aerosol enters the reaction chamber 16, where certain portions of the gas to be examined adsorb on the surface of the particles suspended in the artificially generated aerosol. The interior volume of the reaction chamber 16 is dimensioned such that there is sufficient time for the aforementioned adsorbing reaction to be performed.

Thereafter the aerosol is conducted to a further reaction chamber, in which a pulsed xenon high pressure bulb 17 is arranged. The particles suspended in the aerosol are thereby charged according to their photoelectric activity, and the aerosol finally passes a mechanical filter 11, where the charged particles are collected; accordingly, the resulting current may be measured and recorded. A variation of the mixture rate between the artificially created aerosol and the gaseous substance to be examined will be reflected in a variation of the current measured at the filter 11, and therefrom the concentration and/or the nature of the unknown gas content may be determined.

In order to record such variations of the current, it is not necessary to interrupt the flow of the gas to be examined, since the apparatus may be calibrated to the photoelectric activity of the pure carbon particles. If an inert substance such as silver is used in the aerosol generator, the nitrogen may be replaced by the gas to be examined itself. This removes the need to subsequently admix said gas.

In FIG. 3 there is shown an additional set-up to be used in conjunction with the apparatus set-up shown in FIG. 2 and which is useful in the characterization of gases or gas traces. The aerosol generator 13 and the means 18 for the measurement of the photoelectric activity are interconnected by a tube comprising an inlet 19 near to the outlet of the aerosol generator 13 and an inlet 20 near to the input of the measuring means 18. The inlet 19 is used to admix a gaseous substance which effects a photoelectric activation or disactivation by generating a layer on the particles. The gaseous substance, which is fed through the inlet 20, reacts with this layer with the result that the photoelectric activity is altered again. It is thereby possible either to admix the gas to be examined or a gaseous agent in a first step. Even a simultaneous admixture is possible. In the latter case the reaction at least partially runs already in the gaseous phase.

The set-up according to FIG. 3 enables $O_3$ to be detected very sensitively. By means of the inlet 19, carbon particles are mixed with the vapor of an aromatic hydrocarbon, which, as a layer, increases the photoelectric activity of the particles. If $O_3$ is added through the inlet 20, the photoelectric activity is decreased again by ozonization, if a suitable hydrocarbon is used.

REFERENCES (1) A. Schmidt-Ott and B. Federer; Surface Science 106 (1981), 538
(2) H. Burtscher, L. Scherrer, H. C. Siegmann, A. Schmidt-Ott and B. Federer; J. Appl. Phys. 53(5) 1982
(3) R. Nessner, D. Klockow; J. Aerosol Sci. 13 (1982), 175
(4) H. Burtscher and A. Schmidt-Ott; Sci. Total Environment 36 (1984), 233
(5) For example: Thermo Systems Inc., Aerosol Neutralizer, Model 3012

What we claim is:

1. A method of quantitatively and/or qualitatively analyzing an aerosol by detection of aerosol particles of unknown nature suspended therein, said method comprising the steps of:
   exposing the aerosol to ultraviolet or x-ray radiation to induce photoemission of electrons from at least part of said suspended aerosol particles;
   detecting photoelectric activity of said suspended aerosol particles by determining a photoemission induced first electric charge on said suspended aerosol particles or the electric current corresponding to said first electric charge;
   modifying the photoelectric activity of said suspended aerosol particles; and
   detecting the modified photoelectric activity of said suspended aerosol particles by determining a photoemission induced second electric charge resulting from the modified photoelectric activity of said suspended aerosol particles or the electric current corresponding to said second electric charge.

2. A method according to claim 1 wherein the modification of photoelectric activity is effected by adding a test gas to the aerosol to be analyzed, said test gas comprising at least one component capable of chemical reaction with or of adsorption on the surface of said suspended aerosol particles.

3. A method according to claim 2 wherein said chemical reaction is induced or enhanced by electromagnetic radiation.

4. A method according to claim 2 wherein said test gas component is removed from the aerosol to be analyzed before detecting the modified photoelectric activity.

5. A method of analyzing a gas by qualitatively and/or quantitatively detecting at least one component of the gas by determining photoelectric activity of aerosol particles suspended in the gas, the photoelectric activity of said suspended aerosol particles being modified by the action of said at least one component, said method comprising the steps of:
   determining the presence of aerosol particles of known nature or introducing preselected aerosol particles having a photoelectric activity which is modified by the action of said one component, into the gas to be analyzed;
   exposing the gas to an ultraviolet or x-ray radiation to induce photoemission of electrons from at least part of said suspended aerosol particles;
   determining a photoemission induced electric charge of said suspended aerosol particles or the electric current corresponding to said electric charge.

6. A method according to claim 1 or 5 wherein the modification of the photoelectric activity of the suspended aerosol particles results from at least one chemical reaction or adsorption of at least one substance on the surface of said suspended aerosol particles.

7. A method according to claim 1 or 5 wherein the modification of the photoelectric activity of the suspended aerosol particles results from at least one chemical reaction on the surface of said suspended aerosol particles caused by electromagnetic radiation.

8. A method according to claim 7 wherein the electromagnetic radiation is also used for inducing the photoemission of electrons in said suspended aerosol particles.

9. A method according to claim 1 or 5 wherein a predetermined distribution of charges is effected on the suspended aerosol particles before determining the electric charge or electric current corresponding to the electric charge.

10. A method according to claim 5 wherein preselected aerosol particles are introduced into the gas to be analyzed.

11. A method according to claim 5 wherein aerosol particles of a known nature are suspended in the gas to be analyzed.

12. A method according to claim 11 wherein the aerosol particles of a known nature are produced and suspended in situ within the gas to be analyzed.

* * * * *